United States Patent [19]

Van't Hooft

[11] Patent Number: 5,030,194

[45] Date of Patent: * Jul. 9, 1991

[54] METHOD AND APPARATUS FOR EFFECTING RADIOACTIVE THERAPY IN AN ANIMAL BODY

[75] Inventors: Eric Van't Hooft, Gezichtslaan 16, 3956 BB Leersum; Libbe Van Zwol, Leersum, both of Netherlands

[73] Assignee: Eric Van't Hooft, Leersum, Netherlands

[*] Notice: The portion of the term of this patent subsequent to Nov. 21, 2006 has been disclaimed.

[21] Appl. No.: 436,877

[22] Filed: Nov. 15, 1989

Related U.S. Application Data

[63] Continuation-in-part of Ser. No. 71,835, Jul. 10, 1987, Pat. No. 4,881,937.

[30] Foreign Application Priority Data

Jul. 10, 1986 [NL] Netherlands ................. 8601808

[51] Int. Cl.⁵ ............... A61N 5/00; A61M 37/04
[52] U.S. Cl. ................................. 600/003; 600/7; 250/497.1
[58] Field of Search ................. 600/1, 3, 6, 7; 250/497.1

[56] References Cited

U.S. PATENT DOCUMENTS

| 3,669,093 | 6/1972 | Saverwein et al. | 600/7 |
| 4,233,517 | 11/1980 | Van't Hooft | 600/3 |
| 4,631,415 | 12/1986 | Saverwein et al. | 600/1 |
| 4,733,653 | 3/1988 | Levry et al. | 600/1 |
| 4,851,694 | 7/1989 | Rague | 600/3 |
| 4,881,937 | 11/1989 | Van't Hooft | 600/3 |

FOREIGN PATENT DOCUMENTS

| 0152124 | 8/1985 | European Pat. Off. | 600/7 |
| 3643893 | 6/1988 | Fed. Rep. of Germany | 600/7 |

Primary Examiner—Lee S. Cohen
Assistant Examiner—John D. Zele
Attorney, Agent, or Firm—Griffin Branigan & Butler

[57] ABSTRACT

A first radioactive source assembly disposed in a first source channel and a guide tube connected to the source channel and having a second end which is disposable in the animal body. A first source assembly transport thread connects the first source assembly to a first source assembly drive for driving the first source assembly to the second end of the guide tube. At least one further radioactive source assembly is disposed in a further source channel, a connector tube connects the further source channel and a connector disposed in the guide tube. A juncture is formed at the connector. A further source assembly transport thread is attached to the further source assembly and to a further source assembly drive for driving the further source assembly towards said second end of the said guide tube. The first source assembly and the further source assembly are alternatingly drivable toward the second end of the guide tube. A detector detects the presence of either source assembly in the juncture whereby radiation therapy may be accurately effected by either the first source assembly or the further source assembly.

27 Claims, 4 Drawing Sheets

METHOD AND APPARATUS FOR EFFECTING RADIOACTIVE THERAPY IN AN ANIMAL BODY

This is a continuation-in-part of U.S. patent application Ser. No. 071,835, filed on July 10, 1989, now U.S. Pat. No. 4,881,957, the entire disclosure of which is incorporated herein by reference and relied upon for disclosure herein.

The present invention relates to apparatus and method for effecting radiation therapy in an animal body, e.g. a human, and more particularly to such treatment conducted with apparatus generally known as after-loading devices.

FIELD OF INVENTION

As is well known in the art, localized malignancies may be effectively treated with radiation emitted from a discreet radioactive source placed near that malignancy. The effective treatment, however, is dependent upon the particular malignancy, the position of the malignancy in the body, the activity of the radioactive source, and the accuracy of positioning the radioactive source at the malignancy. Such treatments involve an intrusion into the animal body, e.g. human body, and that intrusion may be through a natural orifice in the body, if the malignancy so admits, or by way of implant needles and other special devices positioned at the malignancy. In either case, the effectiveness of the treatment depends, to a large measure, on accurately placing the radioactive source at the correct position near the malignancy. With some malignancies, a single radioactive source may be sufficient for effective treatment, but with other malignancies, multiple radioactive sources, positioned in and around the malignancy, may be required. In addition, with such multiple positioning of radioactive sources, the amount of radiation for effective treatment may vary with the differently positioned radioactive sources, and therefore, specific regimens of treatment are often necessary in terms of both the positioning of the radioactive source and the duration of radiation exposure of the malignancy.

Since the radioactive sources used in such treatment can constitute a hazard to a technician administering the treatment, devices are now commercially available which allow the positioning of the radioactive source and the treatment therewith in the patient with minimum radiation exposure of the technician or with no exposure whatsoever. These devices allow the positioning of the radioactive source in the patient after the technician administering the treatment moves away from the patient. In other words, the radioactive source is loaded into the patient for treatment after the technician leaves the patient, and these devices are, therefore, generally referred to as "after-loading devices".

Generally speaking, the radioactive sources used with these after-loading devices fall into two categories. The first category is that of a low dose rate (LDR) source, and the second category is that of a high dose rate (HDR) source. An LDR source emits low levels of radiation and can be safely handled by a technician for short periods of time. An HDR source emits high doses of radiation and cannot be safely handled by a technician, even for relatively short periods of time. The after-loading devices for handling these two different radioactive sources are thus divided into two categories of machines, i.e. a low dose rate (LDR) machine and a high dose rate (HDR) machine. In the prior art, an LDR machine is, generally, operated by driving a flexible cable with an LDR source attached to one end from a channel in a safe (radiation shielding block), through a guide tube and to the site of intended therapy in the patient. The correct positioning of the LDR source for effective LDR source therapy is achieved in various manners in the prior art, but the most usual manner is as follows. An applicator, e.g. an implant needle, is positioned by a physician, sometimes surgically, and the correct positioning of that applicator is confirmed by X-ray or fluoroscopic procedures. Thereafter, the patient is moved to a treatment room and the applicator is connected, by appropriate connectors, to an LDR machine. The assumption is that the LDR machine will correctly move the LDR source to the applicator and the LDR source will be reasonably accurately positioned in the applicator. By use of appropriate cable excursion measuring devices, normally associated with an LDR machine, such assumptions are generally justified, and a technician will check the same from time to time. This assumption is further justified since effective treatment with an LDR source often spans many hours, e.g. 20 or 30 or even 50 hours. During such extended treatment, the patient will move in carrying out normal body functions and the LDR source will likewise move in relation to the malignancy. It is assumed that such movements will average out the radiation around the malignancy and, therefore, a very accurate positioning of the LDR source, opposite the malignancy, is not necessary.

In conducting such treatment, the technician administering the treatment is exposed to low levels of radiation, and while this is generally not a substantial problem, especially if the total radiation exposure to the technician is monitored, a hazard does exist.

However, the above assumptions are not always correct and incorrectly positioned LDR sources may result. This results in less effective or ineffective therapy and, in addition, may unnecessarily expose healthy tissue to radiation. Thus, this procedure is less than desirable.

In addition, it is often necessary to employ multiple LDR sources at different sites around the general site of intended therapy, even when treating a single localized malignancy, since a single LDR source does not emit sufficient radiation to effectively treat many, even localized, malignancies. In such case, the same procedure described above is used for each different site of intended therapy, and the above-noted inaccuracies will be compounded.

With high dose rate (HDR) machines, the HDR source is too radioactive for operation in the manner of the LDR machine. In the prior art, the HDR machines are, generally, operated by placing an implant at the correct position for effective therapy and driving the HDR source from its channel until the HDR source is in the correct position in the implant. Various devices have been described in the prior art for determining when the HDR source reaches that correct position in the implant. However, these prior art devices lack desired accuracy, and this desired accuracy is even more of a disadvantage in HDR machines, since exposure of the malignancy to radiation is often only in terms of minutes, e.g. 10, 15 or 20 minutes, and a small inaccuracy in positioning the HDR source can result in large inaccuracies in effective treatment, in view of the short times involved.

BACKGROUND OF THE INVENTION

In the above-mentioned parent application Ser. No. 071,835, an improved HDR machine is disclosed. That application sets forth the general prior art HDR machines and describes those prior art machines as having a radioactive source assembly disposed in a source channel (a channel in a shielding block of conventional design), a guide tube connected to a first end of the source channel, and a second end thereof being disposable in the animal body at the site of intended therapy. A source assembly transport thread (cable) is connected to the source assembly and to a source assembly drive means for driving the source assembly from the source channel and toward the second end of the guide tube, which second end will be the site of intended therapy. This is the same general prior art HDR machine, as described above.

The improvement in that parent application is that of providing a test assembly disposed in a separate test channel. A connector tube connects at a first end to the test channel and at a second end to a connector disposed in the guide tube. Thus, a juncture is formed at the connector between the guide tube and the connector tube. A test assembly transport thread (cable) is attached at one end to the test assembly and at another end to a test assembly drive means for driving the test assembly from the test channel, through the connector tube and connector, and toward the second end of the guide tube. In this arrangement, the source assembly and the test assembly are alternatingly drivable toward the second end of the guide tube. A detector means is provided for detecting the presence of a test assembly or the source assembly in the guide tube between the juncture and the second end of the guide tube.

Thus, in this arrangement, the test assembly is driven through the connector tube and guide tube and past the detector, which is generally at the juncture between the connector tube and the guide tube. The detector will determine when the test assembly passes that juncture. Since the guide tube between the juncture and the site of intended therapy will be a common path for both the test assembly and the source assembly, accurately measuring the excursion of the test assembly from the detector to the site of intended therapy (confirmed by X-ray or the like) will give a very precise measurement of the excursion necessary for the source assembly once that source assembly also passes the detector and into the common pathway guide tube. The guide tube can remain essentially in place on the patient during both when the test assembly is operated and when the source assembly is operated, and, hence, disturbing the common pathway guide tube is not necessary. This gives a very precise positioning of the source assembly for effective radiation therapy and is a substantial improvement over the prior art.

BRIEF DESCRIPTION OF THE INVENTION

The present invention is an improvement of the invention disclosed in the parent application. With the present improvement, the apparatus disclosed in the parent application may be used as either an LDR machine or an HDR machine. This is a decided advantage, since the cost of either of these machines is very high, and the providing of one machine to perform the function of the two separate prior art machines is a distinct operational and economic advantage.

Very broadly, in one aspect of the invention, a low dose rate source is substituted for the test assembly of the apparatus of the parent application. With this change, radioactive therapy may be effected in the animal body, e.g. human patient, by either the high dose rate source or the low dose rate source, as decided upon by the physician. In this latter regard, depending upon the malignancy and the experience of the physician, the physician may choose low dose radiation therapy as opposed to high dose radiation therapy, for a particular patient, and vice versa. From patient to patient, therefore, a physician may require both an LDR machine and an HDR machine, which engenders the additional high expense, as noted above. With the present invention, the single machine can serve both purposes, at least in regard to a number of regimens which may be used for treatment of malignancies.

On the other hand, with the present improvement, if it is desired to use the present apparatus in a method of high dose radiation treatment, the low dose source may be used as a test assembly, in the same manner described in the parent application.

In another aspect of the invention, broadly, in order to allow multiple sites of intended therapy to be serviced by a single machine, the invention departs from the prior art and from the disclosure of the parent application in that an indexer means, which is known to the art, may be disposed between the juncture (the juncture of the guide tube and the connector tube) and the second end of the guide tube so as to provide a plurality of branched guide tubes extending from the indexer to a plurality of sites of intended therapy. (It is, of course, possible to place separate indexers in both the guide tube and the connector tube before the juncture, but this unnecessarily complicates the device and is not preferred.) With the former arrangement, the correct positioning of the HDR source or the LDR source in any one of the branched guide tubes may be determined by using the LDR source as the test assembly, in the manner described in the parent application, and after that correct positioning is determined, the HDR source or the LDR source is serially passed through each of the plurality of guide tubes, in turn, so that the source is positioned serially at different sites of intended therapy around and about the malignancy. By choosing a particular residence time of the HDR source in each of the branched guide tubes, the total radiation provided by the HDR source, with a short residence time, will be equivalent to the radiation provided by a plurality of LDR sources with much longer residence times. In serially passing the HDR source through the plurality of branched guide tubes, a wide area in and around the malignancy can be radiated to effect the same radiation as would have been achieved in a conventional LDR machine with use of a plurality of LDR sources.

Thus, briefly stated, the present invention provides an improvement in known apparatus for effecting radioactive therapy in an animal body, wherein that known apparatus has a first radioactive source assembly disposed in a first source channel, a guide tube connected at a first end to the source channel, and a second end being disposable in the animal body at the site of intended therapy. A first source assembly transport thread (cable) is connected to the first source assembly and to a first source assembly drive means for driving the first source assembly from the first source channel and toward the second end of the guide tube. In the improvement, there is provided at least one further radioactive source assembly disposed in a further source channel. A connector tube is connected at a first end to the further source channel and at a second end to a connector disposed in the guide tube. With this arrangement, a juncture is formed at said connector between the guide tube and the connector tube. A further source assembly transport thread (cable) is attached at one end to the further source assembly and at the other end to a further source assembly drive means for driving the further source assembly from the further source channel, through the connector tube and connector, and toward the second end of the guide tube. With this arrangement, the first source assembly and the further source assembly are alternatingly drivable toward the second end of the guide tube. Also, there is provided a detector means for detecting the presence of the first source assembly or the further source assembly in the guide tube in or between the juncture and the second end of the guide tube. With this arrangement, radiation therapy may be effected in an animal body by either the first source assembly, which will normally be the high dose rate assembly, or by the further source assembly, which will normally be the low dose rate assembly.

The invention also provides a method for effecting radiation therapy in an animal body with that apparatus. The method comprises driving the further source assembly from the further source assembly channel through the guide tube to at least near the second end of the guide tube and at least near the site of intended therapy. The further source assembly is then positioned at the second end of the guide tube so that the position of the further source assembly is at the site of intended therapy. A determination is made of the measured excursion of the further source assembly from the detector means to the site of intended therapy. The further source assembly is then withdrawn from the guide tube and into the further source assembly channel. The first source assembly is then driven from the first source assembly channel, through the guide tube, until the excursion of the first source assembly from the detector means substantially equals the measured excursion of the further source assembly. Thus, the first source assembly is correctly positioned at the site of intended therapy. The first source assembly is then allowed to remain at the site of intended therapy for a predetermined time to effect radiation therapy, and the first source assembly is then withdrawn into the first source assembly channel.

DETAILED DESCRIPTION OF THE INVENTION

Figure 1:
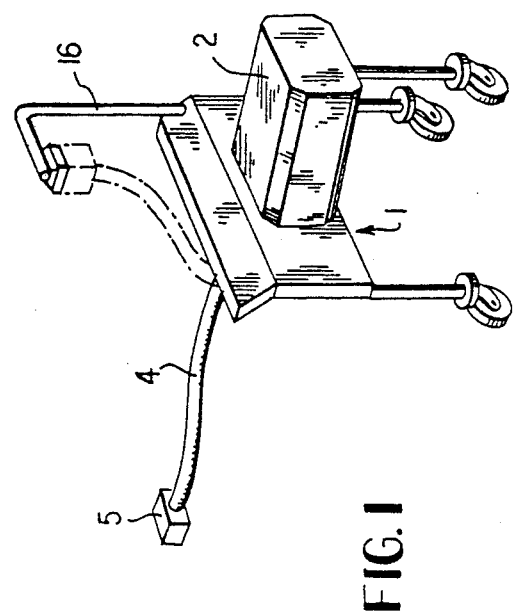
FIG. 1 is a perspective view in diagrammatic form of an embodiment of the present improved apparatus, showing an overall configuration thereof.

As shown in FIG. 1, overall, the apparatus is mounted on a movable frame, generally indicated at 1, and the frame supports a housing 2, which contains the apparatus, as described below. A disconnectable portion of the guide tube 4 is connected to housing 2 at one end thereof, and at the other end thereof is attached to a connector 5, from which another portion of the guide tube extends. The connector 5 is used for connecting the disconnectable portion of the guide tube to the portion of the guide tube which has the second end thereof, e.g. to a portion of the guide tube which is connected to an implant needle or like devices. When the disconnectable portion of the guide tube is not in use, it can be suspended from bracing rod 16, as shown by the dash lines in FIG. 1.

Figure 2:
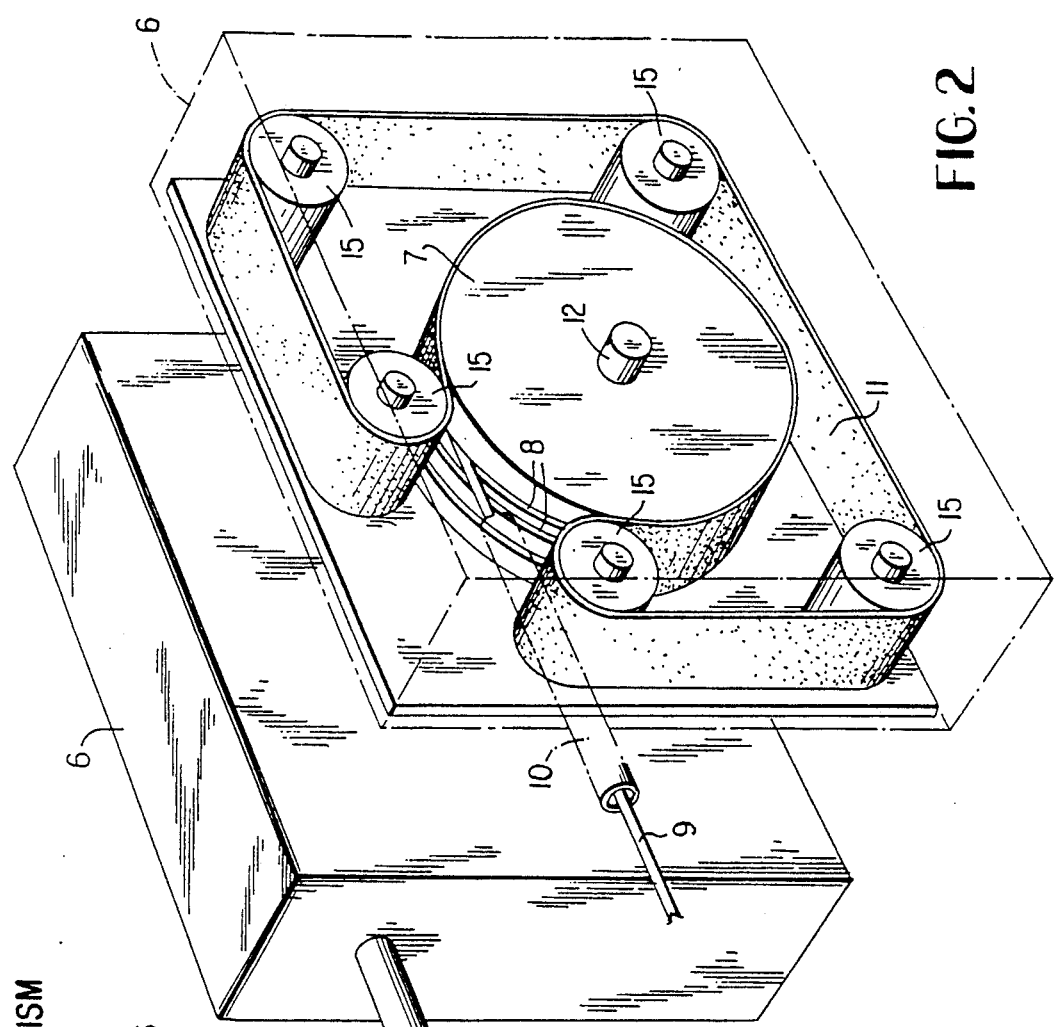
FIG. 2 is a perspective diagrammatic detailed view of a drive means useful in the present apparatus.
Figure 3:
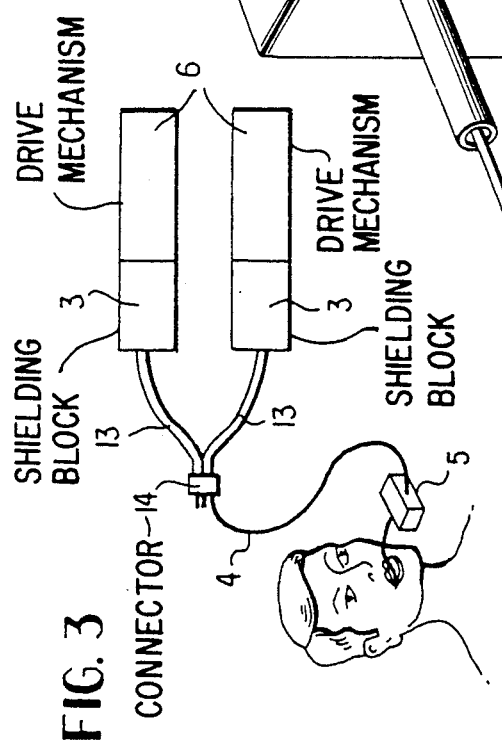
FIG. 3 is a diagrammatic view of the present apparatus arranged for treatment of a human patient.

Housing 2 contains the apparatus shown in FIG. 3, with the exception of guide tube 4. As shown in FIG. 3, that apparatus comprises two drive mechanisms 6 (a detail of the drive mechanism being shown in FIG. 2 and discussed hereinafter) and two snielding blocks 3 containing channels (not shown in FIG. 3) or, alternatively, one shielding block having two channels. Also, within housing 2 are two tubes 13 (described in more detail hereinafter) which are connected to a connector having a detector 14 to form a juncture (described more fully hereinafter). As shown in FIG. 3, the guide tube 4 is connected at one end to the connector having the detector, and the other end is disposed at the site of intended therapy. In the case of FIG. 3, guide tube 4 is disposed through the mouth of the patient and into the lungs for treatment, for example, of a malignancy in the lungs.

Before further discussing the apparatus, in general, attention is first directed to the drive means, shown in FIG. 2, since this is an important mechanical device of the apparatus. FIG. 2 shows only one drive means, but each of the drive means for the first source assembly and the further source assembly are identical. Each drive means consists of a cylindrical disc 7 which has on the outer peripheral or circumferential surface a helical or spirally disposed groove 8 around that surface. That groove is adapted to receive a transport thread 9 (cable), and the transport thread 9 is played off of disc 7 by means of a tubular guide 10. Tubular guide 10 is connected with the channel for the respective assembly (first source assembly or second source assembly—as described more fully hereinafter).

The transport thread 9 is accurately retained in a slip-free manner in groove 8 by means of an endless tensioning belt 11 disposed on contacting means, e.g. the belt passes about rollers 15. The belt 11 contacts the outer peripheral surface of disc 7 through a major portion of that outer peripheral surface, e.g. about 300 angular degrees of that peripheral surface. Disc 7 is driven by a motor 12, which is preferably a stepping motor, for the reasons explained more fully hereinafter. At least one of rollers 15 is preferably spring biased so as to maintain tension on belt 11. The contacting means, e.g. rollers, are contacted by the belt and the belt rolls thereon. The rollers are disposed in relation to the peripheral surface such that the belt is in contact with the surface and is moved around the surface by movement of cylindrical disc 7.

As can be seen, with this type of drive means, very accurate displacement of transport thread 9 is achievable, and that accurate displacement is also important for ensuring proper positioning of a radioactive source, as explained more fully hereinafter.

Figure 4:
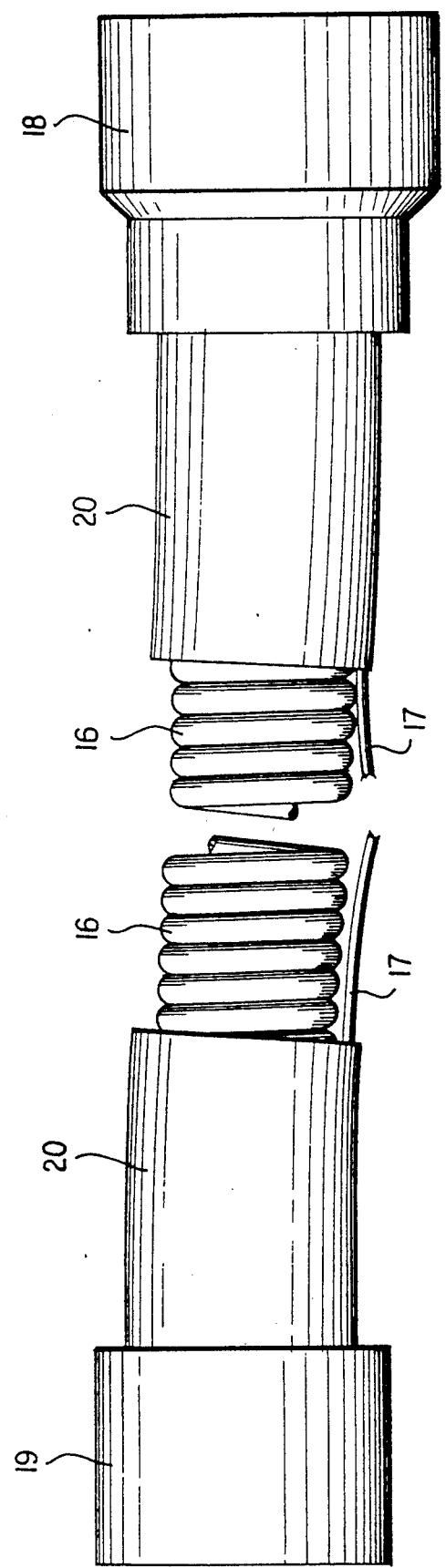
FIG. 4 is an enlarged perspective view of a guide tube useful in the present apparatus, with a portion of the guide tube being removed for clarity purposes.

Also, before discussing the apparatus generally, attention is directed to FIG. 4, which shows a construction of a guide tube. Due to necessary configurations in positioning the guide tube between housing 2 (see FIG. 1) and the site of intended therapy in the patient, as diagrammatically indicated in FIG. 3, that guide tube may necessarily assume a tortuous path. Any kinking in that guide tube could cause binding of transport thread 9 while being driven therethrough, and to avoid such kinking, in view of such necessary tortuous paths, guide tube 4 is preferably constructed in the manner shown in FIG. 4. As shown in that figure, the guide tube has a helically wound metal spring wire 16 having adjoining windings and a longitudinally disposed pull wire 17 disposed along the length of and adjacent the windings of the spring, so as to keep those adjoining windings of spring 16 in close proximity. The pull wire 17 is affixed at its ends to the ends of the guide tube, e.g. to corresponding couplings 18 and 19, which may be male and female couplings, as indicated in FIG. 4. This arrangement will prevent deformation of the guide tube. The spring wire 16 and pull wire 17 are preferably embedded in a sheath of flexible material 20, which may be rubber, synthetic plastic or the like, in order to provide a strong resilient guide tube which will not admit to substantial kinking, even when disposed in tortuous convolutions. The arrangement shown in FIG. 4 also ensures that the guide tube will remain a constant length, even in tortuous configurations, so that the guide tube remains a known length for the reasons explained below.

Figure 5:
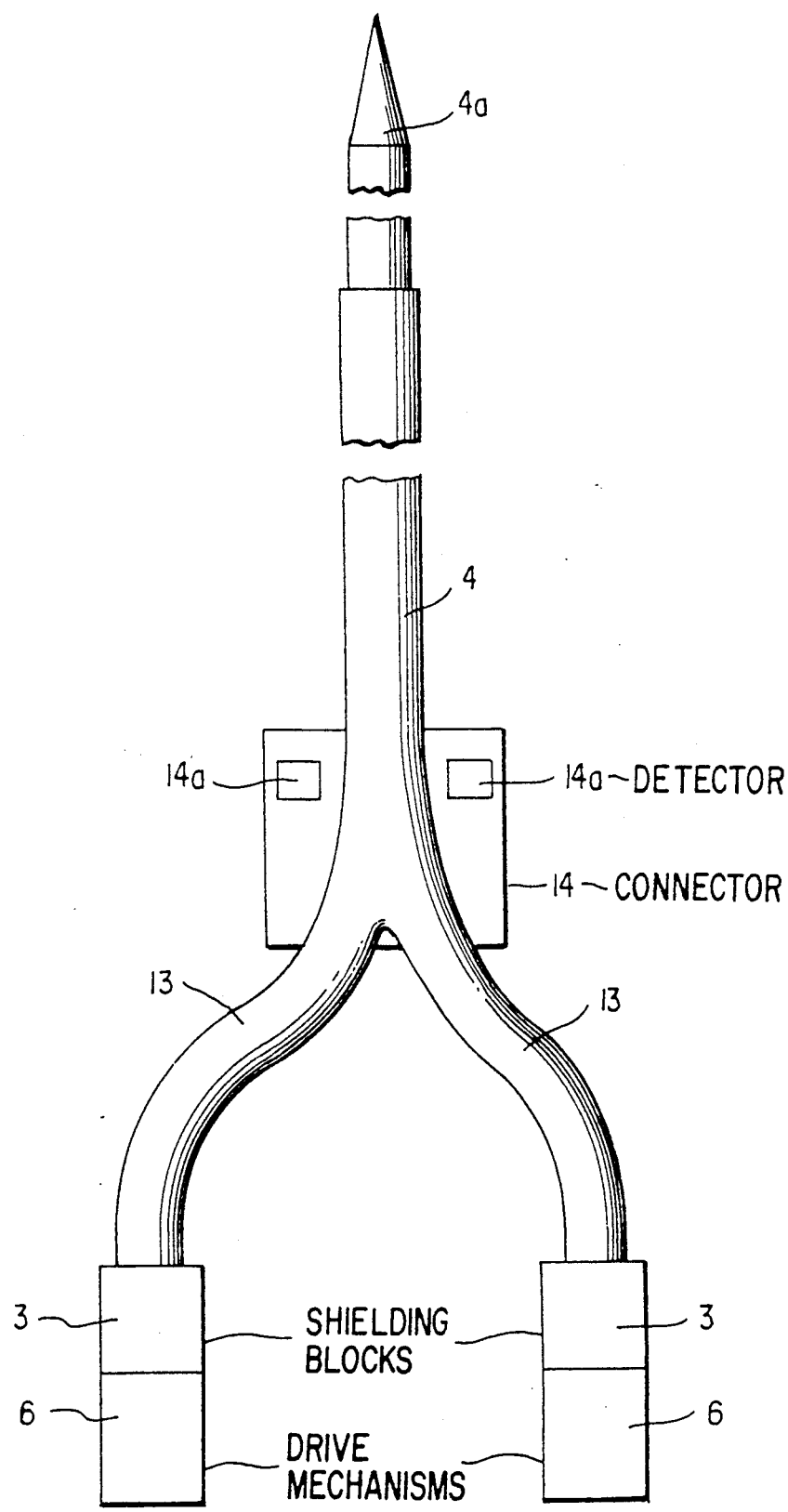
FIG. 5 is an enlarged diagrammatic view of part of FIG. 3, showing more detail of the detector means and connector for the tubes of the apparatus and the use of a hollow needle as part of the second end of the guide tube.

As noted above, FIG. 3 shows two tubes 13 connected to shielding blocks 3 and to a connector having a detector 14, which in turn is connected to guide tube 4. FIG. 5 shows that arrangement in more detail in connection with the connector and detector. Thus, in FIG. 5, two tubes 13 form a juncture at the connector/detector 14, and guide tube 4 extends from the connector/detector 14 to the site of intended therapy. The guide tube 4 may, in part, be comprised of an implant needle 4a when a natural orifice of the body, such as the mouth shown in FIG. 3, is not appropriate for inserting the guide tube to the site of intended therapy. In this latter case, the implant needle 4A may be used for the terminal portion of guide tube 4 so as to allow the positioning thereof at the site of intended therapy, e.g. around the malignancy in a human breast for treating breast cancer. Connector/detector 14 also contains the detector means, e.g. a photoelectric cell 14a for positioning either the first source assembly or the second source assembly, as explained in more detail below.

Figure 6:
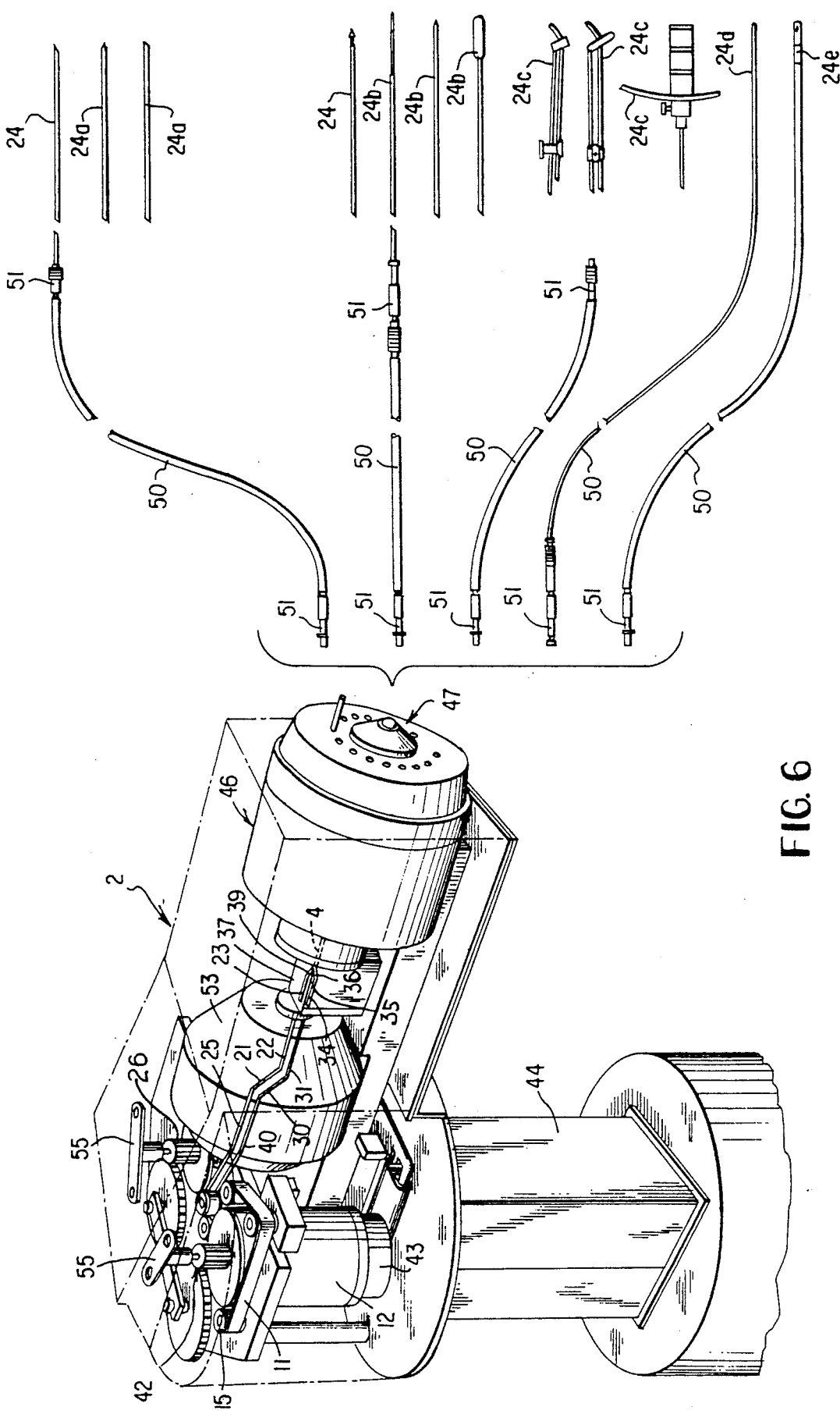
FIG. 6 is a perspective view, partly broken away, showing a further embodiment of the invention where a plurality of branched guide tubes are disposable in the patient for effecting therapy.

FIG. 6 shows a complete embodiment of the invention and includes the various pieces of apparatus, described above, and in a commercially useful layout. As shown in FIG. 6, the apparatus has a first radioactive source assembly 21 disposed in a first source channel 22. A guide tube 23 (one of the tubes 13 shown in FIGS. 3 and 5) is connected at a first end to the first source channel 22 and second end 24 is disposable in the animal body for intended therapy. The second end 24 is shown in FIG. 6 as an applicator, canula or implant needle, e.g. a needle suitable for implantation in the treatment of breast cancer. There is a first source assembly transport thread 25 (shown as 9 in FIG. 2) connected to the first source assembly 21 and to a first source assembly drive means, generally 26, for driving the first source assembly 21 from the first source channel 22 and towards the second end 24 of guide tube 4.

Similarly, FIG. 6 shows a further radioactive source assembly 30 disposed in a further source channel 31, and a connector tube 34 connected at a first end 35 to the further source channel 31 and at a second end 36 to a connector 37 disposed in guide tube 23 to form a juncture 39 at the connector 37 between the guide tube 23 and the connector tube 34. A further source assembly transport thread 40 is attached at one end to the further source assembly 30 and at the other end to the further source assembly drive means, generally 42, which drive means is actuatable for driving the further source assembly 30 from the further source channel 31 through the connector tube 34 and connector 37 and towards the second end 24 of guide tube 4.

The first source assembly drive means 26 and the further source assembly drive means 42 are essentially identical, and as can be seen in connection with further source assembly drive means 42, that drive means has, as also shown in FIG. 2, a drive motor means 12, belt 11, and rollers 15. Of course, the drive means has associated therewith appropriate gearing, journals, switches and stops, as will be appreciated by the art.

While any motor means 12 may be used, it is preferable that the motor means is a stepping electric motor. As is known in the art, a stepping electric motor turns in stepped increments. While only one motor could be used for driving both the first source assembly drive means and the further source assembly drive means, it is preferable that separate stepping motors are independently and operably connected to each of the first source assembly drive means and the further source assembly drive means. Since a stepping motor rotates in known step increments, by use of a conventional shaft encoder 43, the degrees of arc (including the number of revolutions of the stepping motor) can be very accurately determined, in a known manner. The shaft encoder 43 generates a signal, and that signal can be fed to a conventional computer 44 for determining and/or remembering the exact number of revolutions and degrees of arc turned by a stepping motor in driving further source assembly 30 from the detector to the site of intended therapy. By using a stepping motor for driving first source assembly 21, and duplicating the revolutions and degrees of arc used by that stepping motor, as generated by shaft encoder 43, with the revolutions and degrees of arc required by the stepping motor moving the further source assembly from the detector at the site of intended therapy, the computer can very accurately determine and place the first source assembly at the exact site of intended therapy, as briefly explained above, and as more fully explained below. This means of placing the first source assembly at the site of intended therapy is quite accurate in view of the precise playout of the transport threads 25 and 40 from their respective drive means in view of the effect of endless belt 11, as described in connection with FIG. 2 and in view of guide tube 4 accommodating a tortuous path without kinking or longation deformation, as described in connection with FIG. 4, above.

As noted above, it is quite desirable to treat a plurality of intended sites of therapy with a single machine, and to this end, an embodiment of the invention differs from that shown in FIG. 3, where a single guide tube 4 is used. In this preferred embodiment, guide tube 4 (also see 4 in FIG. 6) has a known and conventional indexer means (see U.S. Pat. No. 4,692,628), generally 46, preferably disposed between the juncture 39 and the second end 24 of guide tube 4, and the guide tube is branched at the end of the indexer, generally 47, into a plurality of branched guide tubes 50 attached to the indexer 46. Each of the branched guide tubes has a second end 24 which may be in a variety of forms, including various applicators and including differently shaped implant needles 24a, specifically conformed tubes 24b, specialized applicator devices 24c, catheters 24d, and special tubes 24e, all of which are known. The second end 24, therefore, may be in a configuration suitable for the particular malignancy being treated and suitable for the particular orifice through which second end 24 must either pass or the orifice which must be made by surgery for passage of second end 24.

For convenience, adaptors of various configurations are used for quickly connecting and disconnecting the branched guide tubes 50 to indexer 46 and to the specific configuration of second end 24. Many such adaptors are known in the art, but of particular and most advantageous use are the adaptors disclosed in U.S. patent application Ser. No. 263,937.

As noted above, the indexer is known and need not be described herein, but generally speaking, the indexer functions, by rotation thereof, such that either first guide tube 23 or connector tube 34, through connector 37, can be serially connected to any one of the plurality of branched guide tubes 50. With this arrangement, either the first or further source assembly is drivable from their respective channels, through the indexer means and toward the second end 24 of a selected branched guide tube 50, with that selected branched guide tube 50 being selectable by operation of the indexer means. The indexer 46 is preferably controlled by control means, such as computer 44, for controlling the first and further source assembly drive means and the indexer, in cooperation, such that either source assembly may be serially driven to and disposed at the second end 24 of any selected branched guide tube 50. Here again, the control of the conventional indexer 46 by use of a computer, for selecting branched guide tubes, is known and need not be described herein.

That same controller, e.g. computer 44, will also normally be capable of selecting a residence time during which a source assembly is disposed and resides at a second end 24 of a selected branched guide tube 50 before being withdrawn. By controlling such residence time, a predetermined regimen of radioactive therapy is providable by the apparatus. Indeed, the control means, e.g. computer 44, will normally be capable of selecting a series of such residence times such that a source assembly may have a predetermined residence time in any one of the branched guide tubes 50, and the same or different predetermined residence time may be provided in any other of the branched guide tubes. Thus, variations in radiation therapy from one branched guide tube to another branched guide tube can be provided. This is especially important when using the present apparatus as an LDR machine, as explained more fully below.

Since the second end 24 of each branched guide tube 50 may be of different configuration, as noted above, and since it is important to ensure that the further source assembly and the first source assembly reach the same position in the second end 24, it is preferable that the first source assembly is of substantially the same shape as the further source assembly. This will ensure that the excursion measured by the stepping motors of both the first source assembly and the second source assembly drive means in reaching the site of intended therapy will, indeed, place the source assemblies at the exact same position. For example, when the second end of the branched guide tube 50 is connected to an implant needle, such as one of the implant needles 24a, both the first source assembly and the further source assembly, being of the same shape, are passable into that needle to the same extent. It can be ensured, therefore, that the first source assembly will reside at the exact position as did the further source assembly.

As shown in FIG. 6, the connector 37 is disposed between indexer 46 and shielding block 53, which shielding block contains the first source channel 22 and the further source channel 31, as well as the first source assembly 21 and the further source assembly 30. The shielding block, of course, is of conventional design. As best seen in the diagrammatic illustration of FIG. 5, a detector means 14a is disposed in the connector means 14. Thus, as one of the source assemblies is passed from shielding block 3 through one of tubes 13, that source assembly will be moved into connector 14 and passed detector means 14a disposed therein. While the detector means may be any means for determining when a source assembly passes the detector, preferably the detector means 14a is a photoelectric cell. Thus, when a source assembly passes photoelectric cell 14a, the photoelectric cell signals computer 44 (see FIG. 6) and starts the count of a stepping motor. For example, when photoelectric cell 14a starts the count of stepping motor 12 (see FIG. 6) associated with further source assembly 30, the shaft encoder 43 commences measuring the revolutions and degrees of arc moved by stepping motor 12 in driving further source assembly 30 through the apparatus until it reaches the site of intended therapy at second end 24 of one of branched guide tubes 50. That further source assembly is X-ray film imagable, and therefore, the physician can ensure that the further source assembly has reached the exact position in second end 24 for the desired therapy. After the further source assembly is withdrawn into shielding block 53, the first source assembly drive means 26 is operated by a stepping motor associated therewith (not shown in FIG. 6) and driven past detector means 14a (see FIG. 5), at which time the count of the stepping motor associated with drive means 26 is commenced (see FIG. 6). By operating that stepping motor for the same number of revolutions and degrees of arc as was stepping motor 12, associated with further source assembly drive means 42, after the first source assembly 21 passes detector 14a, it can be ensured that the first source assembly will reach the exact same position in second end 24 as did the further source assembly.

Turning now to preferred methods of operation of the apparatus described above, for effecting radiation therapy in an animal body, e.g. a human, in one embodiment, the further source assembly 30 is driven by drive means 42 from the further source assembly channel 31 through the guide tube 4 to at least near the second end 24 of the guide tube and at least near the site of intended therapy. The further source assembly, in the guide tube, is then positioned, by driving, so that the position of the further source assembly is at the site of intended therapy. This positioning or fine tuning of the position, can be achieved by the physician with use of a fluoroscope or X-ray, since the further source assembly is X-ray film imagable. This positioning can be done in a normal X-ray or fluoroscope room. In this case, the further source assembly would be an LDR source assembly, and since the radiation therefrom is quite low, this fine positioning of the further source assembly can be done with minimum radiation exposure. In reaching that fine positioning, a measured excursion of the further source assembly from the detector means (14a in FIG. 5) when the further source assembly is finely positioned at the site of intended therapy is determined. This determination is made by the shaft encoder 43 connected to stepping motor 12, and that determination is fed into and remembered by the computer 44. The further source assembly is then withdrawn from the guide tube and into the further source assembly channel 31 in shielding block 53.

Subsequently, usually after disconnecting the patient from the machine and moving the patient to a shielded treatment room and reconnecting the patient to the machine, the first source assembly 21 is then driven from the first source assembly channel 22 through the guide tube 4, past detector 14a (see FIG. 5), until the excursion of the first source assembly 21 from the detector means is substantially equal to the measured excursion of the further source assembly, as determined by a shaft encoder associated with the stepping motor connected to the first source assembly drive means 26. By operating that stepping motor to the same number of revolutions and degrees of arc as the stepping motor associated with the further source assembly drive means was operated, it can be ensured that the first source assembly is correctly positioned at the site of intended therapy. However, as noted above, since the first source assembly will be an HDR source assembly, for radiation treatment, the patient will normally be moved from the X-ray or fluoroscope room into a shielded treatment room, before the first source assembly is deployed from shielding block 53. By use of remote controls, known to the art, the technician, from a remote position, can then drive the first source assembly into the patient for effecting radiation therapy as described above.

The first source assembly, which effects the radiation therapy, will remain at the site of intended therapy for a predetermined time, as determined by the treating physician, to effect that radiation therapy. The computer 44 may be programmed to effect that therapy and automatically withdraw the first source assembly back into the first source assembly channel, when the predetermined time has been reached. The computer also allows the use of automatic safety controls. For example, if during treatment, the detector 14a (see FIG. 5) detects movement of the transport thread, e.g. the patient has tampered with the implant needle or a guide tube, then the detector can cause, through computer 44, an automatic withdrawal of the first source assembly back into shielding block 53. Likewise, in the event of a power failure, the computer can withdraw the first source assembly back into shielding block 53 by use of a safety backup battery (now shown in the drawings). Other safety features are the use of one-way hand cranks 55, which may be used in an emergency for hand removal of either the further source assembly or the first source assembly from the patient and back into shielding block 53.

As can be appreciated with the above embodiment of the method of the invention, the first source assembly is a high dose rate radioactive source assembly, used for treatment, and the further source assembly is a low dose rate radioactive source assembly, and the positioning of the further source assembly at the site of intended therapy is determined by X-ray imaging thereof, as a check for the correct positioning of the high dose rate radioactive source assembly when used for treatment purposes.

As a further embodiment of that method, as explained above in connection with the apparatus, the guide tube 4 has an indexer means 46 disposed between the juncture 39 and the second end 24 of the guide tube, and the guide tube is branched, generally at 47, at the indexer means into a plurality of branched guide tubes 50, attached to the indexer means. Also, as explained above, each of the branched guide tubes 50 will have a second end 24, which will be configured as appropriate for the treatment, as noted above. With this arrangement, the process described above is modified in the following regards.

This embodiment of the process has the further steps of serially determining the measured excursion of the further source assembly in a plurality of branched tubes 50 for positioning the further source assembly at a plurality of sites of intended therapy. For example, four branched tubes 50 may have a second end 24 in the form of an implant needle. Those implant needles may be spaced about a breast cancer. The further source assembly is moved into the first of branched tubes 50, until the site of intended therapy in that first implant needle is determined by X-ray or fluoroscope, as described above, and the excursion thereof is determined, as explained above. Then the further source assembly is withdrawn back into shielding block 53, and the excursion of the further source assembly to reach the site of intended therapy in a second of the branched tubes 50 is likewise determined, and so on for all of the branched tubes 50 used in the therapy. Thus, the computer then knows the excursion required for reaching the site of intended therapy in all of the branched guide tubes 50 being used in that therapy.

Thereafter, the first source assembly, which will be an HDR assembly, is driven through the respective branched guide tubes until the excursion of the first source assembly from the detector means substantially equals the measured excursion of the further source assembly in that particular branched guide tube 50. The further source assembly will be allowed to remain in that position for a predetermined time, usually a very short time, which will essentially duplicate the radiation exposure achieved by an LDR source at that position for a much longer time.

The first source assembly is then retracted back into shielding block 53, the indexer 46 is then operated by computer 44 to index the guide tube 4 to a second of the plurality of branched guide tubes 50, and the first source assembly is then driven to the site of intended therapy in the second of the plurality of branched guide tubes 50, and allowed to remain there for a predetermined time, usually simulating LDR radiation, and so on through all of the branched guide tubes 50. With this method, the first source assembly is serially positioned at a plurality of sites of intended therapy and allowed to remain in each of those sites of intended therapy for a predetermined time which will, normally, simulate the radiation that would have been achieved by an LDR source remaining at that site for a much longer time. Indeed, with this method, the predetermined time at which the first source assembly remains at one of the sites of intended therapy may be the same or different as the predetermined time for that source assembly to remain at another of the sites of intended therapy, whereby variations in radiation therapy from one branched guide tube to another branched guide tube may be provided. This allows the physician much more control of the radiation received at a particular site of intended therapy for more effective treatment of the malignancy, e.g. a breast cancer.

As can, therefore, be seen from the above, the present invention allows the present apparatus to be operated either as an LDR source machine or an HDR source machine, and in effect, therefore, combines two machines in one, which provides a substantial economic and operational advantage to the art. In addition, with the use of an HDR source, and a plurality of branched guide tubes, the effective therapy provided by an LDR source machine can be duplicated by the present invention in much shorter time than required by an LDR source machine. On the other hand, the present invention allows the use of the present apparatus as an HDR source machine, but with the ability to accurately determine and place the HDR source at the site of intended therapy. All of this provides a very substantial advantage to the art, and it will be understood that many modifications of the above-described invention will be apparent to those skilled in the art, and it is intended that those modifications be embraced by the spirit and scope of the annexed claims.

What is claimed is:

1. In an apparatus for effecting radiation therapy in an animal body wherein the apparatus has a first radioactive source assembly disposed in a first source channel, a guide tube connected at a first end to said source channel and a second end being disposable in the animal body for the intended therapy a first source assembly transport thread connected to the first source assembly and to a first source assembly drive means for driving the first source assembly from the first source channel and towards the said source end of the guide tube, the improvement comprising at least one further radioactive source assembly disposed in a further source channel, a connector tube connected at a first end to said further source channel, a connector disposed in said guide tube and a second end of the connector tube connected to said connector, wherein a juncture is formed at said connector between said guide tube and said connector tube, a further source assembly transport thread attached at one end to said further source assembly, a further source assembly drive means at an other end of the further source assembly transport thread attached the further source assembly drive means for driving the further source assembly from the further source channel, through the connector tube and connector, and towards said second end of the said guide tube, wherein the first source assembly and the further source assembly are alternatingly drivable toward the second end of the guide tube, and a detector means for detecting the presence of the first source assembly or the further source assembly in the guide tube between the juncture formed at the connector and the second end of the guide tube, whereby radiation therapy may be effected in the animal body by either the first source assembly or the further source assembly.

2. The apparatus of claim 1 wherein the first source assembly is a high dose rate radioactive source assembly and the further source assembly is a low dose rate radioactive source assembly and wherein the further source assembly functions as a test assembly for positioning the first source assembly in the animal body and for effecting low dose radiation therapy in the animal body.

3. The apparatus of claim 1 wherein the guide tube has disposed between said juncture and said second end of the guide tube an indexer means for providing a plurality of branched guide tubes attached to the indexer means and extending to a plurality of sites of intended therapy, with each of said branched guide tubes having a said second end, and wherein either the first or further source assembly is drivable from its respective channel, through said indexer means and towards the said second end of a selected branched guide tube, which selected branched guide tube is selected by operation of said indexer means.

4. The apparatus of claim 3, wherein control means are provided for controlling the first and further source assembly drive means and said indexer means such that either said source assembly may be serially driven to and disposed at the said second end of any selected branched guide tube.

5. The apparatus of claim 4 wherein said control means selects residence times during which said first source assembly and said further source assembly are disposed and reside at said second end of a said selected branched guide tube before being withdrawn therefrom, wherein a predetermined regimen of radioactive therapy is performed.

6. The apparatus of claim 5 wherein said control means selects a series of said residence times wherein said first source assembly and said further source assembly have predetermined residence times in one of said branched guide tubes and the same and different predetermined residence times in other of the said branched guide tubes, wherein variations in radioactive therapy from one branched guide tube to other branched guide tubes are provided.

7. The apparatus of claim 3 including an implant needle and wherein the said second end of a branched guide tube is connected to said implant needle and which implant needle is disposable at the site of intended therapy and the first and further source assemblies are passable into said needle.

8. The apparatus of claim 1 wherein the further source assembly is of substantially the same shape as the first source assembly.

9. The apparatus of claim 1 wherein the said first source assembly drive means and said further source assembly drive means has motor means operably connected thereto for driving said drive means.

10. The apparatus of claim 9 wherein the motor means comprises a stepping motor.

11. The apparatus of claim 10 wherein a separate stepping motor is connected to each of said first source assembly drive means and said further source assembly drive means.

12. The apparatus of claim 1 wherein the said detector means is disposed in said connector.

13. The apparatus of claim 1 wherein the said detector means comprises a photoelectric cell.

14. The apparatus of claim 1 wherein both said source drive means comprise:
    (a) a cylindrical disc having on its outer circumferential surface a groove spirally disposed around said surface and the said source transport thread being disposed in said groove;

(b) an endless belt and contacting means on which said belt is disposed for contacting the belt with a major portion of the said surface and for retaining the said source transport thread in said groove to prevent slipping thereof; and (c) A tubular guide means for passing the said source transport thread to said source channel.

15. The apparatus of claim 14 wherein the said contacting means is a series of rollers upon which the endless belt rolls and said rollers are disposed in relation to said source such that the said endless belt is in contact with said surface and is moved around said major portion of said surface by movement of said cylindrical disc.

16. The apparatus of claim 15 wherein the said major portion of the said surface is at least about 300° of said surface.

17. The apparatus of claim 1 wherein said guide tube has disposed thereabout a helically wound metal spring wire having adjoining winding and said guide tube has disposed thereon a longitudinally disposed pull wire adjacent said windings with the end thereof affixed at the ends of the guide tube wherein the said spring wire and pull wire prevent deformation of the said guide tube.

18. The apparatus of claim 17 wherein the said spring wire and pull wire are embedded in a plastic sheath.

19. The apparatus of claim 1 wherein the said further source assembly is x-ray film imagable.

20. The apparatus of claim 1, including a shielding block and wherein the said first source channel and the said further source channel are disposed in said shielding block.

21. A method for effecting radiation therapy in an animal body at a site of intended therapy, comprising:

(a) driving a further source assembly from a further source assembly channel through a connector tube, a connector and a guide tube to at least near a second end of the guide tube and at least near the site of intended therapy;

(b) positioning the further source assembly in the guide tube so that the position of the further source assembly is at the site of intended therapy;

(c) determining a measured excursion of the further source assembly from a detector means when the further source assembly is positioned at the site of intended therapy;

(d) withdrawing said further source assembly from said guide tube and into the further source assembly channel;

(e) driving a first source assembly from a first source assembly channel, through said connector and said guide tube until the excursion of the first source assembly from said detector means substantially equals the said measured excursion of the further source assembly, whereby the first source assembly is correctly positioned at the site of intended therapy;

(f) allowing the first source assembly to remain at the site of intended therapy for a predetermined time to effect radiation therapy; and (g) withdrawing the first source assembly into the said first source assembly channel.

22. The method of claim 21 wherein the first source assembly is a high dose rate radioactive source assembly and the further source assembly is a low dose rate radioactive source assembly and the positioning of the further source assembly at the site of intended therapy is determined by x-ray imaging thereof.

23. The method of claim 21 wherein the guide tube has disposed between said connector and said second end of the guide tube an indexer means for selecting one of a plurality of branched guide tubes attached to the indexer means, with each of said branched guide tubes having said second end, extending to a plurality of sites of intended therapy, said method comprising the further steps of serially determining the measured excursion of the further source assembly in a plurality of branched guide tubes for positioning the further source assembly at a plurality of sites of intended therapy and thereafter driving the first source assembly in respective branched guides tubes until the excursion of the first source assembly from the detector means substantially equals the measured excursion of the further source assembly, wherein the first source assembly is serially positioned at a plurality of sites of intended therapy.

24. The process of claim 23 wherein the first source assembly resides at each of the plurality of sites of intended therapy for a predetermined time.

25. The process of claim 24 wherein said predetermined time is the same or different, whereby variations in radiation therapy from one branched guide tube to other branched guide tubes are provided.

26. The process of claim 21 wherein both the further source assembly and the first source assembly are driven in stepped increments.

27. The process of claim 21 wherein the guide tube at the second end thereof comprises an implant needle.

* * * * *